US00PP09276P

United States Patent [19]

Cole

[11] Patent Number: Plant 9,276

[45] Date of Patent: Sep. 5, 1995

[54] IMPATIENS PLANT NAMED 'PINK ICE'

[75] Inventor: Douglas S. Cole, Loudon, N.H.

[73] Assignee: D. S. Cole Growers, Inc., Loudon, N.H.

[21] Appl. No.: 262,492

[22] Filed: Jun. 20, 1994

[51] Int. Cl.[6] ..... A01H 5/00

[52] U.S. Cl. ..... Plt./87.6

[58] Field of Search ..... Plt. 87.6

*Primary Examiner*—James R. Feyrer

*Attorney, Agent, or Firm*—Foley & Lardner

[57] ABSTRACT

A new cultivar of *Impatiens sultanii* plant named Pink Ice, characterized by its pink flower color with a darker red-purple throat, its consistent fully double flowers, and its variegated foliage consisting of a medium dark green main color and white edges, the white extending variably from the margin toward the leaf midrib.

1 Drawing Sheet

The present invention comprises a new and distinctive cultivar of Impatiens plant, botanically known as *Impatiens sultanii,* and known by the cultivar name Pink Ice. The species name appears to be synonymous with the species designation *Impatiens wallerana,* also referred to in botanical literature.

The new cultivar is a sport or mutation of the cultivar ROSEBUD ® Lavender, and was discovered by the inventor Douglas S. Cole in November 1993 in a greenhouse in Concord, N.H. The mutation was discovered while taking cuttings of the parent cultivar, when one branch of one plant of the parent cultivar displayed variegated foliage, as opposed to the normal solid green foliage of the parent cultivar. The branch cutting was removed, planted, and grown out, with the variegation and foliage being commonly displayed throughout the plant. Subsequent asexual reproduction by terminal or stem cuttings taken by the inventor in Concord, N.H. has shown that the unique features of this new cultivar are stabilized and are reproduced true to type in successive propagations.

The following characteristics taken in combination distinguish the new cultivar Pink Ice from both its parent and the cultivated *Impatiens sultanii* of this type known and used in the floriculture industry:

1. Consistent fully double flowers which are pink in color.

2. Even growing, well shaped, mounded plant habit. Reasonably self-branching if propagated from a vegetative cutting.

3. Rooting time is approximately seven days to initiate roots at 70° F.; salable cuttings are available in 21 days at 70° F. 4. Cuttings are produced from either tips or sections. The highest quality cuttings are produced by removing approximately a 0.5–1.3 cm tip and discarding it. The remaining cutting then branches much better.

5. The foliage is normally green in the center surrounded by distinct white edges. At times when it is newly potted and growing extremely rapidly the white margin will become thinner and the green center will have a silver sheen over it.

6. The plant flowers in approximately six weeks from a pinched rooted cutting.

7. When left to reach full bloom, the plant is covered with blossoms which are pink in color.

8. Perhaps the most distinguishing feature of Pink Ice over other known double Impatiens cultivars is its clear leaf variegation. The variegation is a very stable white with no yellowing.

The new cultivar is similar in many respects to the parent cultivar ROSEBUD ® Lavender. The primary difference is in the leaf variegation of Pink Ice compared to the solid green leaves of the parent. In addition, Pink Ice is a more compact grower, and takes about a week longer to finish as a fully mature plant when grown in the greenhouse.

The accompanying colored photographs illustrate the overall appearance ofthe new cultivar, showing the colors as true as it is reasonably possible to obtain in colored reproductions of this type.

The top photograph is a front view of a fully grown plant of Pink Ice.

The bottom photograph is a closeup view showing several flowers and variegated foliage.

The illustrated flower color is not correct, and reference is made to the flower color values noted below for the correct color.

The following is a detailed description of my new Impatiens cultivar based on plants produced under commercial practice at Loudon, N.H. Color references are made to the Royal Horticultural Society Colour Chart except where general terms of ordinary dictionary significance are used. The color values were determined during sunny conditions under part naturalo and part inflorescent light in Washington, D.C.

Parentage: Mutation of *Impatiens sultanii,* c.v. ROSEBUD ® Lavender.

Propagation:

A. *Type cutting.*—Tip or section (section is always near tip).

B. *Time to initiate roots.*—7 days at 21° C. summer, 7 days at 21° C. winter.

C. *Rooting habit.*—Good; roots at nodes or internodes; no hormones needed.

Plant description:

A. *Form.*—Mounded form, with some spreading and slight hanging when given space.

B. *Habit of growth.*—Slower, denser growth than its green leaved parent.

C. *Foliage.*—Generally speaking, the foliage color is very unique, being comprised of three colors or shades: green, green with a silver sheen, and a white margin which varies in width, all in varying percentages. 1. Size(mature leaf): Width: 2.5 to 3.0 cm. Length: Approximately 3.0 to 5.0 cm (excluding petiole). 2. Shape: Ovate, tip acuminate. 3. Texture: Smooth with some wrinkling. 4. Margin: Slightly serrated. 5. Color: Mature foliage, top side closest to 137A overlaid with shiny white-grey on surface to provide a grey-green overall effect that is not provided for on the RHS Colour CHart; margins of leaves are white; on immature foliage, top side is similarly closest to 137A, with white irregular margins somewhat wider than on mature leaves. The underside is greyed-green, closest to 191A. The differences in variegation patterns are clearly visible in the photographs, and provide a very attractive appearance. By comparison, the upper surface foliage color of the parent cultivar is a solid 137B. 6. Venation: Not distinctive; veins are generally the same color as surrounding tissue, and are alternate.

Flowering description:

A. Flowering habvit.—Flowers start as a bud the shape of a round ball and the size of a pea, and open similar to a rose in fullness. The flowers open slightly above or even with the foliage.

B. *Flowering season.*—Year-round in greenhouse environment, best in spring.

C. *Flower buds.*—Basically white with a slight touch of light green 145A; pink color comes out as soon as bud cracks open.

D. *Quantity of flowers.*—Varies as to maturity; good flower producer.

E. *Petals.*—Overall inflorescence has an almost rose or camellia type character due to fully double form. 1. Shape: Petals generally round to slightly oblong with indentation in tip. 2. Color: Upper Surface: Mature, 75B with darker 74B throat; main color fades to 75C; immature, between 74D and 75B. Lower surface, mature 75C. 3. Number of petals: Multiple, twenty-five or even more. 4. Size of flowers: 3.0 to 5.0 cm in diameter.

F. *Reproductive organs.*—1. Stamens: Multiple in number; pollen color yellow. 2. Pistils: Stigma color yelow; styles and ovaries not distinctive.

Disease Resistance: Some resistance to Botrytis. Root fungi are seldom a problem.

I claim:

1. A new and distinct cultivar of Impatiens plant named Pink Ice, as illustrated and described.

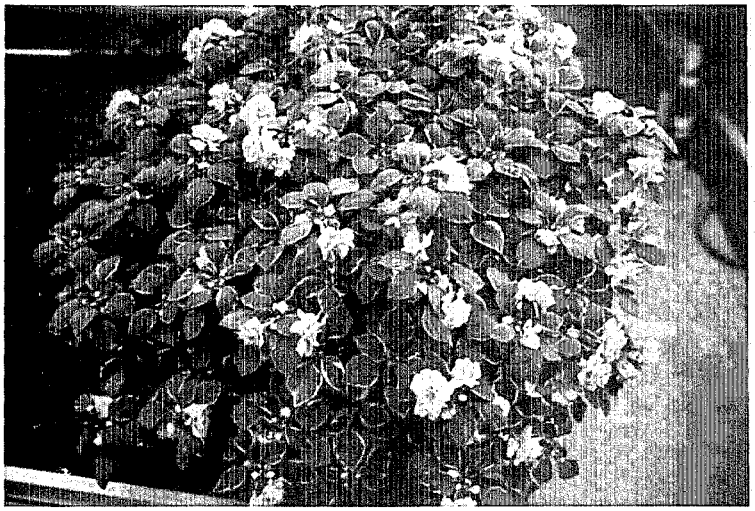
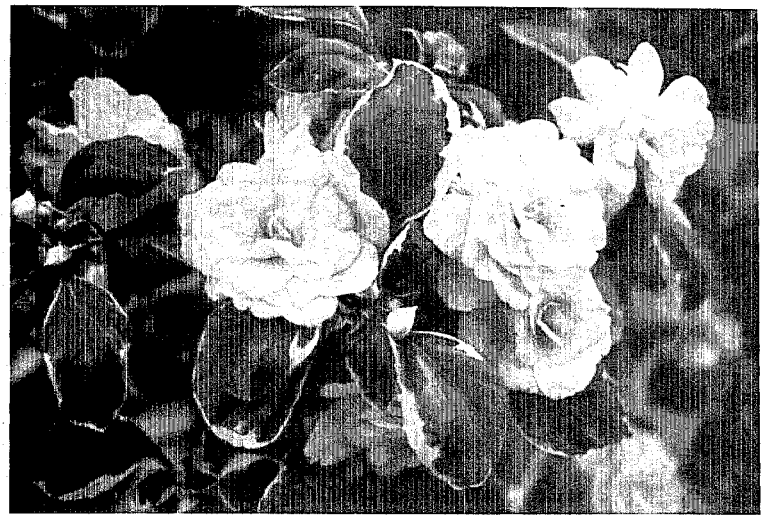

* * * * *